US008143031B2

(12) United States Patent
Figge et al.

(10) Patent No.: US 8,143,031 B2
(45) Date of Patent: Mar. 27, 2012

(54) PRODUCTION OF N-ACYLATED SULPHUR-CONTAINING AMINO ACIDS WITH MICROORGANISMS HAVING ENHANCED N-ACYLTRANSFERASE ENZYMATIC ACTIVITY

(75) Inventors: Rainer Figge, Riom (FR); Guillaume Barbier, Clermont-Ferrand (FR); Gwénaëlle Bestel-Corre, Saint Beauzire (FR)

(73) Assignee: Metabolic Explorer, Saint Beauzire (FR)

( * ) Notice: Subject to any disclaimer, the term of this patent is extended or adjusted under 35 U.S.C. 154(b) by 438 days.

(21) Appl. No.: 12/370,434

(22) Filed: Feb. 12, 2009

(65) Prior Publication Data
US 2010/0047880 A1    Feb. 25, 2010

Related U.S. Application Data

(63) Continuation-in-part of application No. PCT/EP2008/060999, filed on Aug. 22, 2008.

(51) Int. Cl.
*C12N 1/15* (2006.01)
*C12N 1/19* (2006.01)

(52) U.S. Cl. .................................. 435/113; 435/193

(58) Field of Classification Search .................. 435/113, 435/194, 193
See application file for complete search history.

(56) References Cited

U.S. PATENT DOCUMENTS
2005/0026258 A1    2/2005    Ptitsyn et al.

FOREIGN PATENT DOCUMENTS

| EP | 1659174 | 5/2006 |
|---|---|---|
| WO | WO0170776 | 9/2001 |
| WO | WO03023044 | 3/2003 |
| WO | WO2005090589 | 9/2005 |
| WO | WO2007077041 | 7/2007 |
| WO | WO2009043372 | 4/2009 |

OTHER PUBLICATIONS

Davies, et al., I-Methionine Sulfoximine, but Not Phosphinothricin, Is a Substrate for an Acetyltransferase (Gene PA4866) from *Pseudomonas aeruginosa*: Structural and Functional Studies, Biochemistry, 2007, 46 (7), pp. 1829-1839, Publication Date (Web): Jan. 25, 2007.
Durfee, et al., The Complete Genome Sequence of *Escherichia coli* DH10B: Insights into the Biology of a Laboratory Workhorse, Journal of Bacteriology, Apr. 2008, p. 2597-2606, vol. 190, No. 7.
Database UniProt [Online], Mar. 1, 2001, "SubName: Full=Putative uncharacterized protein;" retrieved from EBI accession No. UNIPROT:Q9HUU7, Database accession No. Q9HUU7.
Database EMBL [Online], Jun. 23, 2009, "*Pseudomonas aeruginosa* PAO1, complete genome" Database accession No. AE004091, abstract.
Database Uni Prot [Online], May 20, 2008, "SubName : Full=Predicted acyltransferase with acyl-CoA N-acyltransferase domain;" XP002542267 retrieved from EBI accession No. UNIPROT:BIXDF9, Database accession No. BIXDF9.
Anderson, E.H., Growth Requirements of Virus-Resistant Mutants of *Escherichia coli* Strain "B", Proc Natl Acad Sci U S A. May 1946; 32(5): 120-128.
Baker, David H, Comparative Species Utilization and Toxicity of Sulfur Amino Acids, The American Society for Nutrition J. Nutr. 136:1670S-1675S, Jun. 2006.
Davies, et al., I-Methionine Sulfoximine, but Not Phosphinothricin, Is a Substrate for an Acetyltransferase (Gene PA4866) from *Pseudomonas aeruginosa*: Structural and Functional Studies, Biochemistry, 2007, 46 (7), pp. 1829-1839, Jan. 25, 2007.
Driessen, et al., The mechanism of N-terminal acetylation of proteins, CRC Crit Rev Biochem. 1985;18(4):281-325.
Hippe, et al., Effect of Methionine and N—Acetylmethionine Fortification on the Flavor of Soy Bread and Soy Milk, Journal of Food Science, vol. 43 Issue 3, pp. 793-796, Aug. 25, 2006.
Klein, David C., Arylalkylamine N-Acetyltransferase: "the Timezyme", Feb. 16, 2007, The Journal of Biological Chemistry, 282, 4233-4237.
LaCalle, et al., Molecular analysis of the pac gene encoding a puromycin N-acetyl transferase from *Streptomyces alboniger*, Gene. Jul. 15, 1989;79(2):375-80.
Liebl, et al., Requirement of chelating compounds for the growth of *Corynebacterium glutamicum* in synthetic media, Applied Microbiology and Biotechnology, vol. 32, No. 2 / Dec. 1989, pp. 205-210.
Marvil, et al., N-acetylglutamate synthase of *Escherichia coli*: purification, characterization, and molecular properties. charJ Biol Chem. May 25, 1977;252(10):3295-303.
Polevoda, et al., Nα-terminal Acetylation of Eukaryotic Proteins,The Journal of Biological Chemistry, 275, Nov. 24, 2000, 36479-36482.
Riedel, et al., Characterization of the phosphoenolpyruvate carboxykinase gene from *Corynebacterium glutamicum* and significance of the enzyme for growth and amino acid production, J Mol Microbiol Biotechnol. Oct. 2001;3 (4):573-83.
Schafer, et al., Automated Sampling Device for Monitoring Intracellular Metabolite Dynamics, Analytical Biochemistry, vol. 270, Issue 1, May 15, 1999, pp. 88-96. Tan, et al., Herbicidal inhibitors of amino acid biosynthesis and herbicide-tolerant crops, Amino Acids, vol. 30, No. 2, Mar. 2006, pp. 195-204.
Zahringer, et al., Nourseothricin (streptothricin) inactivated by a plasmid pIE636 encoded acetyl transferase of *Escherichia coli*: location of the acetyl group, FEMS Microbiol Lett. Jul. 1, 1993;110(3):331-4.
Figge, Rainer M., Methionine Biosynthesis in *Escherichia coli* and *Corynebacterium glutamicum*, Microbiology Monographs, vol. May 2007, pp. 163-193.
Carrier, et al., Library of Synthetic 5 Secondary Structures To Manipulate mRNA Stability in *Escherichia coli*, Biotechnology Progress, vol. 15 Issue 1, pp. 58-64, Sep. 4, 2008.

(Continued)

*Primary Examiner* — Tekchand Saidha
(74) *Attorney, Agent, or Firm* — Shweta Chandra; Carol L. Francis; Bozicevic, Field & Francis, LLP

(57) ABSTRACT

The present invention claims an isolated polypeptide having L-amino-acid-N-acyl transferase enzymatic activity and a modified microorganism in which this enzyme is overexpressed. Substrates of said enzyme include mainly methionine and their derivatives or analogs. Overexpression in sulphur-containing amino acid producing microorganisms permits the production of large amounts of N-acylated sulphur-containing amino acids. The isolation of the N-acylated sulphur-containing amino acids from the fermentation medium is also claimed.

17 Claims, 1 Drawing Sheet

OTHER PUBLICATIONS

Choi, et al., Secretory and extracellular production of recombinant proteins using *Escherichia coli*, Applied Microbiology and Biotechnology, vol. 64, No. 5 / Jun. 2004, pp. 625-635.

Datsenko, et al., One-step inactivation of chromosomal genes in *Escherichia coli* K-12 using PCR products, Proc Natl Acad Sci U S A. Jun. 6, 2000;97(12):6640-5.

Gentzen, et al., Aminoacylase from *Aspergillus oryzae*. Comparison with the pig kidney enzyme, Z Naturforsch C. Jul.-Aug. 1980;35(7-8):544-50.

Giardina, et al., The rat kidney acylase I, characterization and molecular cloning Differences with other acylases I, European Journal of Biochemistry, vol. 267 Issue 20, pp. 6249-6255, Dec. 25, 2001.

Jacob-Dubuisson, et al., Protein secretion through autotransporter and two-partner pathways, Biochimica et Biophysica Acta (BBA)—Molecular Cell Research, vol. 1694, Issues 1-3, Nov. 11, 2004, pp. 235-257.

Javid-Majd, et al., Mechanistic analysis of the argE-encoded N-acetylornithine deacetylase, Biochemistry. Feb. 15, 2000;39(6):1285-93.

Jose, et al., The Autodisplay Story, from Discovery to Biotechnical and Biomedical Applications, Microbiology and Molecular Biology Reviews, Dec. 2007, p. 600-619, vol. 71, No. 4, pp. 1092-2172.

Manting, et al., *Escherichia coli* translocase: the unravelling of a molecular machine, Molecular microbiology 2000;37 (2):226-38.

Shokri, et al., Cell and process design for targeting of recombinant protein into the culture medium of *Escherichia coli*, Appl Microbiol Biotechnol. Feb. 2003;60(6):654-64. Epub Dec. 14, 2002.

Mountain, et al. Cloning of a *Bacillus subtilis* restriction fragment complementing auxotrophic mutants of eight *Escherichia coli* genes of arginine biosynthesis. Mol Gen Genet. 1984;197(1):82-9.

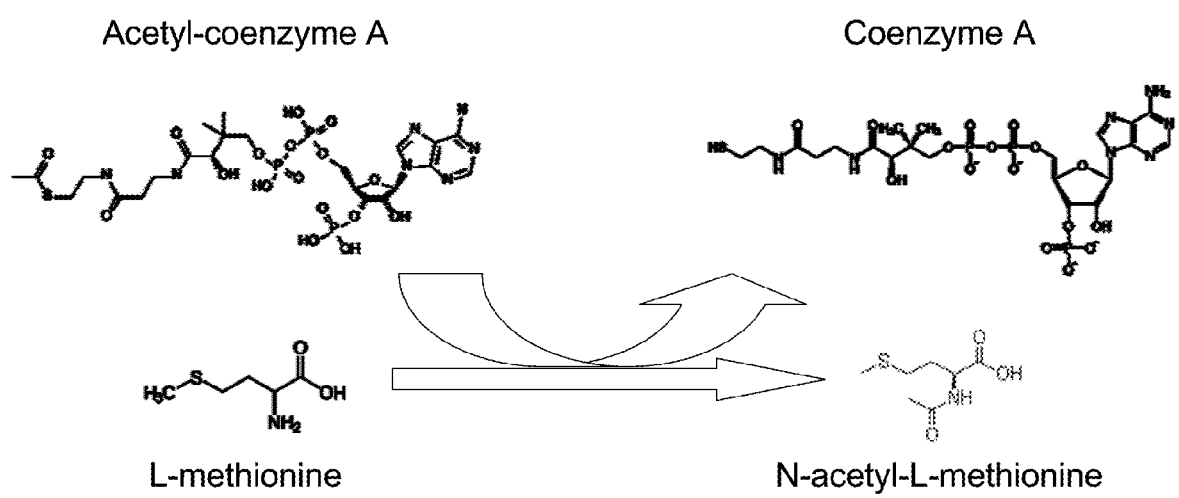

US 8,143,031 B2

PRODUCTION OF N-ACYLATED SULPHUR-CONTAINING AMINO ACIDS WITH MICROORGANISMS HAVING ENHANCED N-ACYLTRANSFERASE ENZYMATIC ACTIVITY

CROSS-REFERENCE TO RELATED APPLICATION

This application is a continuation-in-part of PCT application serial no. PCT/EP2008/060999, filed Aug. 22, 2008 in English and designating the United States.

FIELD OF THE INVENTION

The present invention claims an isolated polypeptide having L-amino-acid-N-acyl transferase enzymatic activity and a modified microorganism in which this enzyme is overexpressed. Substrates of said enzyme include methionine and its derivatives or analogs. Overexpression in sulphur-containing amino acid producing microorganisms permits the production of large amounts of N-acylated sulphur-containing amino acids. The isolation of the N-acylated sulphur-containing amino acids from the fermentation medium is also claimed.

INTRODUCTION

N-acyl transferases catalyze the transfer of an acyl group, usually from the acyl donor acyl-coenzyme A, to an amino group. An acyl group is a functional group derived from a carboxylic acid of the form RCOOH. It has the formula RC(=O)—, with a double bond between the carbon and oxygen atoms (i.e. a carbonyl group), and a single bond between R and the carbon. Examples of acyl groups are: formyl (CH2=O), acetyl (C2H4=O) propionyl (C3H6=O) and butyryl (C4H8=O) groups.

N-acyl transferases are important enzymes in prokaryotes and eukaryotes and are involved in processes such as biological timing (Klein D C, 2007, J Biol Chem, 282(7):4233-7), antibiotic resistance (Zahringer et al., 1993, FEMS Microbiol Lett., 110(3), 331-4; Lacalle R A, et al., 1989, Gene 79(2): 375-80) and resistance to herbicides. In plants, acylation of phosphinotricin catalyzed by the gene products 'Bar' and 'Pat' leads to glufosinate resistance (Tan W. et al., 2006, Amino Acids, 30(2):195-204).

Some N-acyl-transferases catalyze specifically the transfer of groups such as formyl or acetyl, and are so-called "N-formyl-transferase" or "N-acetyl-transferase". Other transferases have a more general catalytic activity and are simply called "N-acyl-transferases".

N-terminal acetylation of methionine, as a co-translational process, is one of the most common protein modifications in eukaryotes. However, acetylases that recognize the N-terminus of a polypeptide do not recognize methionine as a free amino acid (for review see Polevoda & Sherman 2000 JBC 275, 47, pp 36479-36482). In prokaryotes, methionine acetylation as a co-translational process is rare (Driessen et al. 1985, CRC Crit. Rev. Biochem. 18, 281-325).

N-Acylating enzymes, which possibly could acylate methionine as a free amino-acid, have been described. For example, ArgA encodes an N-acetyl-glutamate synthase in *E. coli* (Marvil & Leisinger 1977 JBC 252, 10 pp. 3295-3303). Whereas N-Acetylation of methionine derivatives such as methionine sulfoximine and methionine sulfone (Davies et al., 2007, Biochemistry, 46(7), pp 1829-39) has been described, enzymes that have a significant acylating activity for free methionine are currently not known.

N-acetyl-L-methionine (NAM) is a derivative of methionine that has been acetylated on the amino group. NAM has been shown to have the same methionine-sparing value as pure methionine (Baker, 2006, Journal of Nutrition 136, pp. 16705-55). It has also been included into soy bread or soymilk, where it performs better than pure methionine with respect to sensory detection (Hippe & Warthesen, 1978, Journal of food science 43(3) pp 793-6).

Chemical biosynthesis of N-acetylmethionine produces a racemate of the D- and L-stereo-isomers and it is known that N-acetyl-D-methionine is not incorporated as well as its L-isomer by animals. Deracemization is an expensive process making the production of NAM non-profitable. Therefore, the fermentative production of pure N-acetyl-L-methionine for food/feed and pharmaceutical applications would be an economically viable process.

Another important derivative of methionine is N-propionyl-L-methionine (hereafter NPM), wherein methionine has been propionylated on the amino group.

Products resulting from the acylation of L-methionine have been shown to be advantageous for wool production of sheep (U.S. Pat. No. 4,093,740 entitled "Propionyl-methionine: Fodder for ruminants") and for the production of cosmetic products (U.S. Pat. No. 3,624,114 entitled "Fatty Acid Amido-Methionine Products").

SUMMARY

The present invention is related to an isolated polypeptide having an L-amino-acid-N-acyl transferase enzymatic activity, comprising the sequence of SEQ ID NO: 1, a fragment or a homologous sequence thereof. More specifically the isolated polypeptide has L-amino-acid-N-acyl transferase activity for the substrates methionine, lysine and glutamate, their derivatives and analogs.

The present invention is also related to modified microorganisms having an L-amino-acid-N-acyl transferase activity that is modified, in particular enhanced. Said microorganisms show an increased production of N-acylated amino acids compared to the production observed in a non-modified microorganism.

BRIEF DESCRIPTION OF THE DRAWINGS

FIG. 1 represents the N-acetylation of L-methionine to N-acetyl-L-methionine as catalyzed by the enzyme YncA using Acetyl-coenzyme A as a cofactor.

DETAILED DESCRIPTION OF THE INVENTION

The present invention is related to an isolated polypeptide having an L-amino-acid-N-acyl transferase enzymatic activity, comprising the sequence of SEQ ID NO: 1, a fragment or a homologous sequence thereof.

The isolated polypeptide has been shown to present L-amino-acid-N-acyl transferase activity for the substrates methionine, lysine, glutamate, their derivatives and analogs.

As used herein, the following terms may be used for the interpretation of the claims and specification.

According to the invention, the term "polypeptide" refers to peptide or protein which comprises a sequence of two or more amino-acids linked with peptide bonds.

The term "isolated" refers to a protein or DNA sequence that is removed from at least one component with which it is naturally associated.

The terms "enzyme activity" and "enzymatic activity" are used interchangeably and refer to the ability of an enzyme to catalyse a specific chemical reaction, for example the conversion of methionine into NAM for methionine N-acetyl transferase enzyme activity.

The term 'L-amino acid N-transacylase enzymatic activity or L-amino-acid-N-acyl transferase activity" designates the addition of an acyl group to the amino group of a substrate, e.g. the addition of an acyl group to the amino group of the amino acid methionine (see FIG. 1). Preferentially the acyl group is a butyryl, more preferentially it is a propionyl and in an even more specific embodiment it is an acetyl group.

Derivatives or analogs of methionine, lysine, or glutamate are defined as methionine sulfoximine, homocysteine, methionine sulfone, methionine sulfoximine glutamine or phosphinotricin (glufosate).

The isolated polypeptide of the present invention can be obtained from microorganisms having methionine N-acyl transferase activity, for example by using the purification procedure as described in the following examples. Microorganisms that can be used to isolate the polypeptide include, but are not limited to E. coli.

The term "comprising the sequence of SEQ ID NO: 1" means that the amino-acid sequence of the polypeptide may not be strictly limited to SEQ ID NO: 1 but may contain additional amino-acids. The term "a fragment of SEQ ID NO: 1" means that the sequence of the polypeptide may include fewer amino-acids than SEQ ID NO: 1 but still enough amino-acids to confer L-amino-acid-N-acyl transferase activity. It is well known in the art that a polypeptide can be modified by substitution, insertion, deletion and/or addition of one or more amino-acids while retaining its enzymatic activity. For example, substitutions of one amino-acid at a given position by a chemically equivalent amino-acid that does not affect the functional properties of a protein are common. For the purpose of the present invention, substitutions are defined as exchanges within one of the following groups:

Small aliphatic, non-polar or slightly polar residues: Ala, Ser, Thr, Pro, Gly

Polar, negatively charged residues and their amides: Asp, Asn, Glu, Gln

Polar, positively charged residues: H is, Arg, Lys

Large aliphatic, non-polar residues: Met, Leu, Ile, Val, Cys

Large aromatic residues: Phe, Tyr, Trp.

Thus, changes that result in the substitution of one negatively charged residue for another (such as glutamic acid for aspartic acid) or one positively charged residue for another (such as lysine for arginine) can be expected to produce a functionally equivalent product. The positions where the amino-acids are modified and the number of amino-acids subject to modification in the amino-acid sequence are not particularly limited. The man skilled in the art is able to recognize the modifications that can be introduced without affecting the activity of the protein. For example, modifications in the N- or C-terminal portion of a protein may be expected not to alter the activity of a protein under certain circumstances.

The term "homologous" refers to polypeptides submitted to modifications such as defined above while still retaining the original enzymatic activity.

According to the invention, the polypeptide having an L-amino-acid-N-acyl transferase enzymatic activity may comprise a sequence having at least 70% identity with the sequence shown in SEQ ID NO: 1, preferentially at least 80% identity, and more preferentially at least 90% identity.

Methods for the determination of the percentage of identity between two protein sequences are known from the man skilled in the art. For example, it can be made after alignment of the sequences by using the software CLUSTALW available on the website www.ebi.ac.uk/clustalw/ with the default parameters indicated on the website. From the alignment, calculation of the percentage of identity can be made easily by recording the number of identical residues at the same position compared to the total number of residues. Alternatively, automatic calculation can be made by using for example the BLAST programs available on the website www.ncbi.nlm-.nih.gov/BLAST/ with the default parameters indicated on the website.

According to the invention, the polypeptide having an amino acid N-acyl transferase enzymatic activity may comprise at least 100 contiguous amino acids from the sequence of SEQ ID NO: 1, preferentially at least 120, at least 140, at least 160 or more preferentially at least 172 contiguous amino-acids of the sequence shown in SEQ ID NO: 1.

In another embodiment of the invention, the polypeptide having an L-amino acid N-acyl transferase enzymatic activity has a polypeptide sequence strictly identical to the sequence of SEQ ID NO: 1.

The invention is also relative to a polynucleotide comprising a sequence coding for the polypeptide of the invention. Inventors report the identification of a gene from E. coli encoding a protein having L-amino-acid-N-acyl transferase activity for the substrates methionine, lysine, glutamate, methionine sulfoxide, methionine sulfone, methionine sulfoximine, aspartate and asparagine. This gene was previously known as yncA in E. coli, identified during the complete genome analysis of E. coli. This gene was already reported as a putative acyltransferase, but no specific function has been demonstrated yet (ecogene.org). It was also reported as a Mar-regulated gene in a method that identifies compounds that modulate the expression of Mar-regulated genes, known to be involved in multidrug resistance (WO 01/70776).

The term "polynucleotide" refers to a polymer of ribonucleotides (or RNA) or to a polymer of deoxyribonucleotides (or DNA), that is single or double-stranded, optionally containing synthetic, non-natural, or altered nucleotide bases. An isolated polynucleotide in the form of DNA may contain one or more segments of synthetic DNA, genomic DNA or cDNA.

The origin of the polynucleotide is not necessarily the organism where the enzymatic activity is originally measured. Hybridization under different conditions of stringency with a probe that comprises the nucleotide sequence of SEQ ID NO: 2 can be used by the man skilled in the art to screen a gene library for such polynucleotides. Detailed protocols for hybridization are disclosed in Sambrook et al. (1989).

The sequences of such polynucleotides can be extracted from the databases using for example the BLAST programs defined above and searching for homology with the nucleotide sequence of SEQ ID NO: 2 or searching with the polypeptide sequence of SEQ ID NO: 1 and retrieving the corresponding polynucleotide sequence(s).

Preferred polynucleotides of the present invention are polynucleotides that are at least 60% identical to the nucleotide sequence of SEQ ID NO: 2. More preferred polynucleotides of the present invention are polynucleotides that are at least 80% identical to the nucleotide sequence of SEQ ID NO: 2. More preferred nucleotides are at least 90% identical to the nucleotide sequence of SEQ ID NO: 2. Even more preferred polynucleotides of the present invention are polynucleotides that are at least 95% identical to the nucleotide sequence of SEQ ID NO: 2.

In particular, the polynucleotide that comprises the nucleotide sequence of SEQ ID NO: 2 is included in the invention.

The terms "encoding" or "coding" refer to the process by which a polynucleotide, through the mechanisms of transcription and translation, produces an amino-acid sequence. This process is allowed by the genetic code, which is the relation between the sequence of bases in DNA and the sequence of amino-acids in proteins. One major feature of the genetic code is to be degenerate, meaning that one amino-acid can be coded by more than one triplet of bases (one "codon"). The direct consequence is that the same amino-acid sequence can be encoded by different polynucleotides. As an example, polynucleotide sequences derived from SEQ ID NO: 2 by degeneracy of the genetic code can also code for the polypeptide sequence of SEQ ID NO: 1 and are therefore contemplated by the present invention. It is well known to the man skilled in the art that the use of codons can vary in different organisms. Among the codons coding for the same amino-acid, some can be used preferentially by a given microorganism. It can thus be of interest to design a polynucleotide adapted to the codon usage of a particular microorganism in order to optimize the expression of the corresponding protein in this organism.

The present invention is also related to an expression cassette comprising the polynucleotide of the invention under the control of regulatory elements functional in a host microorganism.

The term "expression" refers to the transcription and translation of a gene sequence leading to the generation of the corresponding protein, product of the gene.

The term "expression cassette" refers to a polynucleotide preferably linked to regulatory elements, such as promoters, enhancers, ribosome binding site or terminator allowing the expression of the gene contained in the polynucleotide inside a suitable host organism. Such regulatory elements can be the own regulatory elements of the gene, but also modified or synthetic elements, to allow a stronger expression of the gene. For example, stronger expression can be obtained by replacing the native promoter of the gene by stronger promoters. For *E. coli* these promoters are for example: lac promoter, tac promoter, trc promoter and lambda cI promoter. For other organisms, the skilled artisan may be able to choose the most appropriate.

The term "host microorganism" refers to a microorganism able to receive foreign or heterologous genes or extra copies of its own genes and able to express these genes to produce an active protein product.

The invention is also relative to a transformation vector comprising the expression cassette according to the invention, or the polynucleotide of the invention.

The term "transformation" refers to the introduction of DNA, e.g. new genes or extra copies of existing genes into a host organism. The acquired genes may be incorporated into chromosomal DNA or introduced as extra-chromosomal elements. As an example, in *E. coli*, a method for transferring DNA into a host organism is electroporation.

The term "transformation vector" refers to any vehicle used to introduce a polynucleotide in a host organism. Such vehicle can be for example a plasmid, a phage or other elements known by the expert in the art according to the organism used. In addition to the polynucleotide or the expression cassette the transformation vector usually contains other elements to facilitate the transformation of a particular host cell. An expression vector comprises an expression cassette allowing the suitable expression of the gene harboured by the cassette and additional elements allowing the replication of the vector in the host organism. An expression vector can be present at a single copy or at multiple copies in the host organism.

In a specific embodiment of the invention, a vector or an isolated DNA fragment is introduced into the microorganism, said vector or fragment permitting the chromosomal integration of the cassette or the polynucleotide according to the invention. The man skilled in the art knows different useful vectors for chromosomal integration of a gene.

The invention provides also a modified microorganism having modulated L-amino-acid-N-acyl transferase enzymatic activity, wherein the activity of the polypeptide having L-amino-acid-N-acyl transferase activity according to the invention, is enhanced.

The term "modified microorganism" denotes a microorganism that has been genetically modified with the goal to increase the accumulation of N-acylated products in the fermentation broth. The man skilled in the art knows how to modulate the expression of specific genes. Usual modifications include transforming microorganisms with genetic elements, including deletions of genes, gene replacements, modification of promoters, and introduction of vectors for the expression of heterologous genes.

The term "activity of a polypeptide" denotes an enzymatic activity, characterized by the transformation of a substrate into a final product that is measurable and correlates directly with the activity of the L-amino-acid-N-acyl transferase catalyzing the reaction.

The "enhanced activity" for the N-acyl transferase polypeptide of the invention means that the production of the N-acylated product, particularly sulphur-containing aminoacid, with the transformed microorganism is increased compared to the same microorganism prior to modification.

Enhanced activity for the N-acyl transferase polypeptide of the invention can be obtained by any means such as preparing and expressing a variant having increased activity or, more particularly, by overexpressing the said polypeptide. Overexpression can be obtained by different means known in the art such as modulating the expression of the factors influencing the expression of the native gene coding for said polypeptide, if present. It can also be obtained by modifying the promoter of said native gene, if present, with regulatory elements allowing stronger expression of the gene product, such elements being known in the art, such as enhancers, or eventually using known strong promoters. Over expression can also be obtained by introducing a new gene with a sequence coding for the polypeptide of the invention under control of a strong promoter, eventually with multiple copies of said gene.

All techniques for transforming the microorganisms, and regulatory elements used for enhancing production of the protein of the invention are well known in the art and available in the literature, including applicant's own patent applications on modification of biosynthesis pathways in various microorganisms, including WO2008/052973, WO2008/052595, WO2008/040387, WO2007/144346, WO2007/141316, WO2007/077041, WO2007/017710, WO2006/082254, WO2006/082252, WO2005/111202, WO2005/073364, WO2005/047498, WO2004/076659, the content of which is incorporated herein by reference.

More particularly, the enhanced level of production of the N-acylated product, can be measured in the culture medium.

The level of production/accumulation of N-acylated product in the medium is assayed. The accumulation of the N-acylated product is increased by at least by 20% preferentially 50%, more preferentially 75% and even more preferentially 95% of the amount accumulated in the same process with a non-modified organism.

The amount of accumulated NAM is determined in the fermentation broth using refractometric HPLC, using NAM (Sigma, Ref 01310) as a standard. The amount of N-propionyl-methionine is determined in the fermentation broth using GC-MS, using NAM (Sigma, Ref 01310) as a standard.

In a specific embodiment of the invention, the expression of at least one other acyltransferase is increased in the modified microorganism of the invention. Such enzymes and theirs coding sequences are known in the art, including ArgA (N-acetylglutamate synthase), YjdJ, YfaP, YedL, YjhQ. At least expression of one of these genes is increased, meaning that increase of combinations of these genes is also contemplated in the microorganism of the present invention.

In another embodiment of the invention, the activity of genes catalyzing the deacylation of acylated amino acids is attenuated. Attenuating the activity of said genes, known in the art, is obtained preferably by attenuating their expression. Particularly, the expression of the argE gene, coding for an enzyme catalyzing NAM deacetylation, is attenuated.

In another specific embodiment of the invention, the expression of at least one gene involved in methionine biosynthesis is increased. Genes involved in methionine biosynthesis have been extensively described in patent applications such as WO 2007/077041 and WO 2005/108561, incorporated herein by reference.

Preferentially, the microorganism of the invention is selected among the group consisting of bacteria, yeast and fungi. More preferentially, the bacterium is selected among the group consisting of Enterobacteriaceae, Bacillaceae, Streptomycetaceae and Corynebacteriaceae. More preferentially, the microorganism is a species of *Escherichia, Klebsiella, Pantoea, Salmonella, Bacillus* or *Corynebacterium*. Even more preferentially, the bacterium is selected among the species consisting of *Escherichia coli* and *Corynebacterium glutamicum*.

The invention also concerns a method for the production of an N-acylated aminoacid in a medium, comprising contacting said aminoacid with a polypeptide having an L-amino-acid-N-acyl transferase enzymatic activity as disclosed above and below, in presence of acyl-coenzyme A and recovering the N-acylated aminoacid. The medium is defined as any medium in which the enzymatic activity can occur. It generally consists of water solutions having a pH adapted for an optimum activity of the enzyme.

The person skilled in the art can select the most appropriate conditions to allow this catalytic transformation.

The invention is also related to a method for the production of N-acyl sulphur-containing amino acids by culturing a microorganism according to the invention, in an appropriate culture medium comprising a source of carbon, a source of sulfur and a source of nitrogen, and recovering the N-acylated sulphur-containing amino acid from the culture medium.

In a specific embodiment of the invention the produced N-acylated sulphur-containing amino acid is N-acetyl-methionine. In another embodiment of invention the produced N-acylated amino acid is N-propionyl-methionine.

An 'appropriate culture medium' is a medium appropriate for the culture and growth of the microorganism, said medium comprising a source of carbon, a source of sulfur and a source of nitrogen. Such media are well known to the person skilled in the art in microorganism fermentation, depending upon the microorganism being cultured.

The term 'carbon source' according to the present invention denotes any source of carbon that can be used by those skilled in the art to support the normal growth of a microorganism, which can be hexoses (such as glucose, galactose or lactose), pentoses, monosaccharides, disaccharides (such as sucrose, cellobiose or maltose), oligosaccharides, molasses, starch or its derivatives, hemicelluloses, glycerol and combinations thereof. An especially preferred simple carbon source is glucose. Another preferred simple carbon source is sucrose.

In a specific embodiment of the invention, the carbon source is derived from renewable feed-stock. Renewable feed-stock is defined as raw material required for certain industrial processes that can be regenerated within a brief delay and in sufficient amount to permit its transformation into the desired product.

Specifically, the nitrogen source is either an ammonium salt or an ammoniac gas. The nitrogen source may be supplied in the form of ammonium or ammoniac.

The sulphur source used for the fermentative production of L-methionine, its precursors or compounds derived thereof, may be any of the following: sulfate, thiosulfate, hydrogen sulfide, dithionate, dithionite, sulfite, methylmercaptan, dimethyldisulfide or a combination thereof.

In a preferred embodiment of the invention, the sulphur source is sulfate and/or thiosulfate.

The fermentation is generally conducted in fermenters with an appropriate culture medium adapted to the microorganism being used, containing at least one simple carbon source, and if necessary co-substrates necessary for the production of metabolites.

As an example of known culture medium for *E. coli*, the culture medium can be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

As an example of known culture medium for *C. glutamicum*, the culture medium can be of identical or similar composition to BMCG medium (Liebl et al., 1989, *Appl. Microbiol. Biotechnol.* 32: 205-210) or to a medium such as described by Riedel et al. (2001, *J. Mol. Microbiol. Biotechnol.* 3: 573-583).

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

In a specific embodiment of the invention, the method comprises as a further step the isolation of the desired N-acylated amino acids from the reaction medium, constituents of the fermentation broth and/or from the biomass, optionally remaining in portions or in the total amount (0-100%) in the final product.

In a specific embodiment of the invention, the method comprises limiting or starving the microorganism for phosphate and/or potassium.

In a particular embodiment of the invention, the recovered acylated amino acid is selected among N-acetyl-methionine and N-propionyl-methionine.

EXAMPLES

Example 1

Purification of MNAT (Methionine N-acyl transferase) Activity

MNAT Activity Test In Vitro

Methionine L-amino-acid-N-acyl transferase activity was followed in microtiter plates by monitoring the apparition of HS-CoA with DTNB. The reaction solution, to which the sample was added, contained 200 mM Tris-HCl, pH 9.0, 100 mM DTNB, 3 mM Acetyl-coA and 20 mM methionine. Formation of the DTNB-CoA complex was monitored at 408 nm using a µQuant microtiter plate reader (BioTek Instruments, Inc., USA).

MNAT Purification

~3 g of dry weight cells were rinsed 3 times with extraction buffer (EB) (50 mM phosphate, pH 7.0, 50 µM PLP, 500 µM DTT) and suspended in 70 mL EB. Cells were broken by sonication using a Rosett cell with a Bandelin Sonoplus ultrasonic homogenizer (Bandelin Electronic, Germany) equipped with a UW2070 probe and a SH70G tip (6 burst, 30 s, 100% efficiency, 75 W). The crude extract was centrifuged (30 min, 12.000 g, 4° C.) and solid ammonium sulfate was added to the supernatant to a final concentration of 2.3 M, and incubated on ice for 30 min. The solution was centrifuged (15 min, 15.000 g, 4° C.) and the pellet suspended in 40 mL phosphate buffer (50 mM phosphate, pH 7.0). Solid ammonium sulfate was added to a final concentration of 1.5 M, and the solution was incubated on ice for 30 min and then centrifuged (15 min, 15.000 g, 4 C). The supernatant was further processed using the AKTA purifier unit (Amersham Biosciences, USA) and its software (Unicorn software, Amersham Biosciences, USA). The solution was then subjected to a Phenyl-HP column (GE Healthcare Bio-Sciences AB, Sweden) previously equilibrated with 10 bed volumes of phosphate buffer. Protein was eluted with a 1.5 to 0 mM ammonium sulfate gradient in phosphate buffer at a 1 mL/min flow rate. The fraction with the most activity was obtained at ~0.5 mM ammonium sulfate and dialyzed overnight at 4° C. against 20 mM Tris pH 7.0 buffer. It was then subjected to anion chromatography using a ResourceQ column (GE Healthcare Bio-Sciences AB, Sweden) equilibrated with 10 bed volumes of 20 mM Tris pH 7.0 and eluted with a 20 mM Tris pH 7.0 NaCl gradient buffer ranging from 0 to 0.5 M NaCl at a 2 mL/min flow rate. The fraction with most of the activity eluted at an NaCl concentration of ~0.25 M. Prior to the gel filtration step, the protein solution was concentrated using an Amicon ultra 15 filter (Millipore Corporation, USA). The concentrated extract was passed through a Superdex 200 column (GE Healthcare Bio-Sciences AB, Sweden) equilibrated with two bed volumes of a 20 mM tris, 150 mM NaCl buffer. The fraction containing most MNAT activity was obtained at an elution volume of ~15.3 mL, corresponding to a molecular weight of 36 kDa. Finally, the protein solution was applied on a Bio-scale ceramic hydroxylapatite column (Bio-Rad Laboratories, USA) previously equilibrated according to the manufacturer's instructions and eluted using a 10 to 500 mM phosphate buffer gradient (pH 6.8) at a flow rate of 2 mL/min. The fraction with most activity was obtained at an elution concentration of ~130 mM phosphate. Denaturing SDS gel electrophoresis of the different fractions showed that during the purification a ~17 kDa band was enriched.

TABLE 1

Enrichment of methionine N-acyl transferase by purification. Indicated are the increase in specific activity, total purified activity, purification yield and purification factor.

| Steps | Specific Activity (mUI/mg prot) | Activity (UI) | Yield | Purification Factor |
|---|---|---|---|---|
| Centrifuged Crude Extract | 21 | 5.234 | 100 | — |
| Purified Protein | 19689 | 0.126 | 2 | 958 |

Band Analysis

After SDS gel electrophoresis the band at 17 kDa region was excised and subjected to trypsin digestion. The digested protein was analyzed by nanoLC-MS/MS on a CapLC-Q-TOF2 (Waters Corporation, USA) and results were processed with ProteinLynx Global Server (Waters Corporation, USA) and Mascot (Matrix Science). The purified protein was identified as YncA, a GCN5 related acyl transferase. Sequence is shown in SEQ ID NO: 1. YncA has 63% identity with PA4688 from *Pseudomonas aeruginosas*, a N-acetyl-methionine sulfoximine transferase. It had been shown that *Pseudomonas* PA4866 protein did not acetylate L-methionine (Davies et al., Biochemistry, 2007).

Example 2

Determination of YncA Substrate Specificity

Substrate Specificity Test

The substrate specificity was tested using the DTNB-based assay (see above).

Substrate Specificity

Strong activities were observed with methionine sulfone, methionine sulfoxide methionine sulfoximine and methionine respectively. Weak activities were obtained with lysine, glutamate, glutamine, aspartate and asparagine.

The preferred acyl-donor with methionine as substrate was propionyl-CoA. Acetyl-CoA also worked properly as an acyl donor in these conditions, while butyryl-CoA gave weak activities with methionine as substrate.

TABLE 2

Substrate specificity determined with the DTNB-based method using Acetyl-coA as acyl-donor. Shown are various substrates, their corresponding activity with respect to the substrate methionine in percent and the total specific activity in mUI/mg protein

| Substrate | % Activity | Specific Activity |
|---|---|---|
| Methionine | 100 | 745 |
| Lysine | 1.6 | 12 |
| Methionine sulfoximine | 166.9 | 1243 |
| Methionine sulfoxide | 147.6 | 1100 |
| Methionine sulfone | 178.8 | 1332 |
| Glutamate | 0.6 | 4 |
| Glutamine | 1.4 | 10 |
| Aspartate | 1 | 7 |
| Asparagine | 2.4 | 18 |

TABLE 3

Activity of YncA with various acyl-donors. The acyl-donor specificity was determined with the DTNB-based method using methionine a as substrate. Shown are various co-substrates, the corresponding activity of YncA with respect to the co-substrate Acetyl-coA in percent and the total specific activity in mUI/mg protein

| Substrate | % Activity | Specific Activity |
|---|---|---|
| Acetyl-coA | 100 | 745 |
| Propionyl-coA | 140% | 1039 |
| Butyryl-coA | 17% | 129 |

Example 3

Overexpression of yncA

Construction of the Plasmid pSCB-CI857-PlambdaR-yncA

The plasmid pSCB-CI857-PlambdaR-yncA is derived from the vector pSCB (Stratagene). For the construction of the pSCB-CI857-PlambdaR-yncA vector, the pSCB-CI857-PlambdaR and pSCB-yncA plasmids are constructed first. The CI1857-PlambdaR fragment is PCR amplified from the pFC1 plasmid (Mermet-Bouvier and Chauvat, 1994) using the following oligonucleotides, CI857-PlambdaR-F and CI857-PlambdaR-R:

```
CI857-PlambdaR-F:
                                        (SEQ ID NO: 3)
ACCTTGCCGAGGGCCCTAAAAATAAGAGTTACCTTAAATGGTAACTCTTA TTTTTTTTAtcagccaaacgtctcttcaggcc
``` with
- a region homologous to the CI857 region (lower case)
- a region for the addition of an ApaI restriction site (bold upper case) with extrabases (upper case)

```
CI857-PlambdaR-R
                                        (SEQ ID NO: 4)
GCATTTGCCACTGATGTACCGCCGAACTTCAACACTCTcatatgacctcc ttagtacatgc
``` with
- a region homologous to the PlambdaR region (lower case) encompassing a NdeI restriction site with extra-bases (upper case)

The PCR amplified fragment is cloned into the pSCB vector (Stratagene). Recombinant plasmids are verified by DNA sequencing, resulting in the pSCB-CI857-PlambdaR plasmid.

Then, the yncA fragment (SEQ ID No2) is PCR amplified from genomic DNA of *E. coli* MG1655 using the following oligonucleotides, YncAF and YncAR (reference sequence on the website ecogene.org):

```
YncAF:
                                        (SEQ ID NO: 5)
TCCCCCGGGGAGCTGTTGACAATTAATCATCCGGCTCGTATAATGTGTGG

AATTGTGAGCGGATAACAATTTCACACTAAGGAGGTATCATatgtccatc cgttttgcccgc
``` with
- a region (lower case) homologous to the yncA region from 1516870 to 1516850
- a region for the addition of an NdeI restriction site, overlapping the ATG of the yncA gene (bold case)

```
YncAR:
CGGGATCCtcatccaatcgcgtccggttc           (SEQ ID NO: 6)
``` with
- a region (lower case) homologous to the yncA region from 1516352 to 1516372
- a BamHI restriction site (bold upper case) with extra bases (upper case).

The PCR amplified fragment is cloned into the pSCB vector (Stratagene). Recombinant plasmids are verified by DNA sequencing, resulting in the pSCB-yncA plasmid. The pSCB-CI857-PlambdaR and pSCB-yncA plasmids are cut with the restriction enzymes NdeI and BamHI, and the fragment containing yncA is cloned into the NdeI/BamHI sites of the pSCB-CI857-PlambdaR plasmid, resulting in the plasmid pSCB-CI857-PlambdaR-yncA.

Construction of the Strain MG1655 metA*11 ΔmetJ Ptrc-metH Ptrc36-ARNmst17-metF PtrcF-cysPUWAM PtrcF-cysJIH ApykA ΔpykF Ptrc09-gcvTHP ΔpurU (pME101-thrA*1-cysE-PgapA-metA*11) (pCC1BAC-serB-serA-serC) (pSCB-CI857-PlambdaR-yncA)

The plasmid pSCB-CI857-PlambdaR-yncA is introduced into a methionine-producing strain, the MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU (pME101-thrA*1-cysE-PgapA-metA*11) (pCC1BAC-serB-serA-serC) strain, already described in patent application PCT/EP2007/060433, giving rise to the strain MG1655 metA*11 ΔmetJ Ptrc-metH Ptrc36-ARNmst17-metF PtrcF-cysPUWAM PtrcF-cysJIH Ptrc09-gcvTHP ΔpykA ΔpykF ΔpurU (pME101-thrA*1-cysE-PgapA-metA*11) (pCC1BAC-serB-serA-serC) (pSCB-CI857-PlambdaR-yncA).

Example 4

Evaluation of Methionine Producing Strains with Increased Accumulation of NAM or NPM Production strains are evaluated in small Erlenmeyer flasks. A 5.5 mL preculture is grown in a mixed medium at 30° C. (10% LB medium (Sigma 25%) with 2.5 g.L$^{-1}$ glucose and 90% minimal medium PC1—WO 2007/077041) and is used to inoculate a 50 mL culture to an OD$_{600}$ of 0.2 in minimal medium PC1 cultivated at 37° C. Kanamycin and spectinomycin are added if needed at a concentration of 50 mg.L$^{-1}$, ampicillin at 100 mg L$^{-1}$, chloramphenicol at 30 mg.L$^{-1}$. When the culture has reached an OD$_{600}$ of 6 to 7, extracellular amino acids are quantified by HPLC after OPA/Fmoc derivatization and other relevant metabolites are analyzed using HPLC with refractometric detection (organic acids and glucose) and GC-MS after silylation. The test is repeated three times.

NON-PATENT REFERENCES

Klein D C, 2007, J Biol Chem, 282(7):4233-7),
Zähringer et al., 1993, FEMS Microbiol Lett., 110(3), 331-4,
Lacalle R A, et al., 1989, Gene 79(2):375-80),
Tan W. et al., 2006, Amino Acids, 30(2):195-204),
Polevoda & Sherman 2000 JBC 275, 47, pp 36479-36482),
Driessen et al. 1985, CRC Crit. Rev. Biochem. 18, 281-325,
Marvil & Leisinger 1977 JBC 252, 10 pp. 3295-3303,
Davies et al., 2007, Biochemistry, 46(7), pp 1829-39,
Baker, 2006, Journal of Nutrition 136, pp. 16705-55,
Hippe & Warthesen, 1978, Journal of food science 43(3) pp 793-6,
Anderson, 1946, *Proc. Natl. Acad. Sci. USA* 32:120-128,
Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.),
Schaefer et al. (1999, *Anal. Biochem.* 270: 88-96,
Liebl et al., 1989, Appl. Microbiol. Biotechnol. 32: 205-210,
Riedel et al. (2001, J. Mol. Microbiol. Biotechnol. 3: 573-583,
Davies et al., Biochemistry, 2007.

The invention claimed is:

1. A modified microorganism having an enhanced L-amino-acid-N-acyl transferase enzymatic activity, wherein the activity of a polypeptide, having L-amino-acid-N-acyl transferase enzymatic activity and comprising a sequence having at least 90% sequence identity with SEQ ID NO: 1, is enhanced as compared to the activity of the enzyme in an unmodified microorganism.

2. The microorganism of claim 1, wherein the expression of at least one other acyl transferase is increased.

3. The microorganism of claim 2, wherein said other acyltransferase is selected among the group consisting of N-acetylglutamate synthase (ArgA), YjdJ, YfaP, YedL, YjhO and combinations thereof.

4. The microorganism of claim 1, wherein the activity of genes catalyzing deacylation of acylated amino acids is attenuated.

5. The microorganism of claim 4, wherein said gene catalyzing the deacylation of acylated amino acid is argE.

6. The microorganism of claim 1, wherein the expression of at least one gene involved in methionine biosynthesis is increased.

7. The microorganism of claim 1, wherein said microorganism is selected among the group consisting of bacteria, yeast and fungi.

8. The microorganism of claim 7, wherein the bacterium is selected among the group consisting of Enterobacteriaceae, Bacillaceae, Streptomycetaceae and Corynebacteriaceae.

9. The microorganism of claim 8, selected among the group consisting of Escherichia coli and Corynabacterium glutamicum.

10. A method for the production of N-acylated sulphur-containing amino acids, comprising culturing a microorganism according to claim 1, in an appropriate culture medium comprising a source of carbon, a source of sulphur and a source of nitrogen, and recovering the N-acylated sulphur-containing amino acid from the culture medium.

11. A method for the production of N-propionylated amino acid, comprising culturing a microorganism according to claim 1, in an appropriate culture medium comprising a source of carbon, a source of sulphur and a source of nitrogen, and recovering the N-propionylated sulphur-containing amino acid from the culture medium.

12. A method for the production of N-acetylated amino acid, comprising culturing a microorganism according to claim 1, in an appropriate culture medium comprising a source of carbon, a source of sulphur and a source of nitrogen, and recovering the N-acetylated sulphur-containing amino acid from the culture medium.

13. The method of claim 10, wherein the sulphur source is chosen among the group consisting of sulphate, thiosulfate, hydrogen sulphide, dithionate, dithionite, sulfite, methylmercaptan, dimethyldisulfide and a combination thereof.

14. The method of claim 13 wherein the sulphur source is sulphate or thiosulfate, and mixture thereof.

15. The method of claim 10, wherein the carbon source is derived from a renewable feed-stock.

16. The method of claim 10, wherein the carbon source is glucose or sucrose.

17. The method of claim 10, wherein the nitrogen source is supplied in the form of ammonium or ammoniac.

* * * * *

UNITED STATES PATENT AND TRADEMARK OFFICE
CERTIFICATE OF CORRECTION

PATENT NO. : 8,143,031 B2
APPLICATION NO. : 12/370434
DATED : March 27, 2012
INVENTOR(S) : Rainer Figge et al.

It is certified that error appears in the above-identified patent and that said Letters Patent is hereby corrected as shown below:

Column 15, Line 52, replace "(ArgA)" with -- ArgA --;

Column 16, Line 41, replace "*Corynabacterium*" with -- *Corynebacterium* --.

Signed and Sealed this
Nineteenth Day of February, 2013

Teresa Stanek Rea
*Acting Director of the United States Patent and Trademark Office*

SEQUENCE LISTING

<160> NUMBER OF SEQ ID NOS: 6

<210> SEQ ID NO 1
<211> LENGTH: 172
<212> TYPE: PRT
<213> ORGANISM: Escherichia coli

<400> SEQUENCE: 1

Met Ser Ile Arg Phe Ala Arg Lys Ala Asp Cys Ala Ala Ile Ala Glu
1               5                   10                  15

Ile Tyr Asn His Ala Val Leu Tyr Thr Ala Ala Ile Trp Asn Asp Gln
            20                  25                  30

Thr Val Asp Ala Asp Asn Arg Ile Ala Trp Phe Glu Ala Arg Thr Leu
        35                  40                  45

Ala Gly Tyr Pro Val Leu Val Ser Glu Glu Asn Gly Val Val Thr Gly
    50                  55                  60

Tyr Ala Ser Phe Gly Asp Trp Arg Ser Phe Asp Gly Phe Arg His Thr
65                  70                  75                  80

Val Glu His Ser Val Tyr Val His Pro Asp His Gln Gly Lys Gly Leu
                85                  90                  95

Gly Arg Lys Leu Leu Ser Arg Leu Ile Asp Glu Ala Arg Asp Cys Gly
            100                 105                 110

Lys His Val Met Val Ala Gly Ile Glu Ser Gln Asn Gln Ala Ser Leu
        115                 120                 125

His Leu His Gln Ser Leu Gly Phe Val Val Thr Ala Gln Met Pro Gln
    130                 135                 140

Val Gly Thr Lys Phe Gly Arg Trp Leu Asp Leu Thr Phe Met Gln Leu
145                 150                 155                 160

Gln Leu Asp Glu Arg Thr Glu Pro Asp Ala Ile Gly
                165                 170

<210> SEQ ID NO 2
<211> LENGTH: 519
<212> TYPE: DNA
<213> ORGANISM: Escherichia coli

<400> SEQUENCE: 2
atgtccatcc gttttgcccg caaagccgac tgtgctgcca ttgcggaaat ttataaccac      60
gccgtgttgt atacggcggc tatctggaat gaccaaacgg tggatgctga taaccgcatt     120
gcctggtttg aagcgcggac tttagcaggt tatccagtgc tggtgagcga ggaaaacggc     180
gtagtgacgg gatatgcctc gtttggcgac tggcgtagtt tcgatggttt tcgccatacc     240
gtggaacatt cggtttatgt ccatcccgat catcagggca aaggtctggg gcgtaaattg     300
ttaagccgat tgattgatga agcgcggat tgcgggaagc atgtcatggt cgccgggatc     360
gaatcgcaaa atcaggcctc gctgcatctc caccagtcgc tgggatttgt cgtcaccgcg     420
caaatgccgc aggtaggcac taaatttggt cgttggctgg atctgacatt tatgcagttg     480
caactcgacg agcgcactga accggacgcg attggatga                            519

<210> SEQ ID NO 3
<211> LENGTH: 82
<212> TYPE: DNA
<213> ORGANISM: Artificial
<220> FEATURE:
<223> OTHER INFORMATION: Oligonucleotide

<400> SEQUENCE: 3

```
accttgccga gggccctaaa aataagagtt accttaaatg gtaactctta ttttttttat      60
cagccaaacg tctcttcagg cc                                              82

<210> SEQ ID NO 4
<211> LENGTH: 61
<212> TYPE: DNA
<213> ORGANISM: Artificial
<220> FEATURE:
<223> OTHER INFORMATION: Oligonucleotide

<400> SEQUENCE: 4
gcatttgcca ctgatgtacc gccgaacttc aacactctca tatgacctcc ttagtacatg      60
c                                                                     61

<210> SEQ ID NO 5
<211> LENGTH: 29
<212> TYPE: DNA
<213> ORGANISM: Artificial
<220> FEATURE:
<223> OTHER INFORMATION: Oligonucleotide

<400> SEQUENCE: 5
cgggatcctc atccaatcgc gtccggttc                                       29

<210> SEQ ID NO 6
<211> LENGTH: 112
<212> TYPE: DNA
<213> ORGANISM: Artificial
<220> FEATURE:
<223> OTHER INFORMATION: Oligonucleotide

<400> SEQUENCE: 6
tcccccgggg agctgttgac aattaatcat ccggctcgta taatgtgtgg aattgtgagc      60
ggataacaat ttcacactaa ggaggtatca tatgtccatc cgttttgccc gc             112
```